United States Patent [19]

Schneider

[11] Patent Number: 4,945,908
[45] Date of Patent: Aug. 7, 1990

[54] BALNEO-PHOTOTHERAPEUTICAL TREATMENT PROCESS AND BATH

[76] Inventor: Karl Schneider, Ostlandstrasse 12, D-6427 Bad Salzschlirf, Fed. Rep. of Germany

[21] Appl. No.: 240,383

[22] Filed: Aug. 29, 1988

Related U.S. Application Data

[63] Continuation of Ser. No. 928,086, Nov. 7, 1986, abandoned.

[30] Foreign Application Priority Data

Nov. 7, 1985 [EP] European Pat. Off. ........ 85114154.9

[51] Int. Cl.$^5$ .......................................... A61H 33/00
[52] U.S. Cl. ................... 128/369; 128/396; 128/66; 210/169; 4/539; 4/546
[58] Field of Search ............... 128/369, 372, 395, 396, 128/365, 371, 373, 64, 66, 24.1; 4/539, 546, 559, 545, DIG. 10, 524; 210/169

[56] References Cited

U.S. PATENT DOCUMENTS

| | | | |
|---|---|---|---|
| 2,057,208 | 10/1936 | Runcie | 210/169 |
| 2,208,291 | 7/1940 | Halpern et al. | 128/395 |
| 2,292,666 | 9/1940 | Schurtz | 128/369 |
| 3,366,110 | 1/1968 | Gaylord | 128/369 |
| 3,885,557 | 5/1975 | Varea | 128/365 |
| 3,943,580 | 3/1976 | Carter | 210/169 |
| 4,130,120 | 12/1978 | Kohler | 128/373 |
| 4,200,360 | 4/1980 | Mutzhas | 128/372 |
| 4,277,855 | 7/1981 | Poss | 128/371 |
| 4,339,833 | 7/1982 | Mandell | 128/66 |
| 4,424,598 | 1/1984 | Cima | 4/524 |
| 4,469,102 | 9/1984 | Fish | 128/395 |
| 4,563,780 | 1/1986 | Pollack | 4/546 |

FOREIGN PATENT DOCUMENTS

| | | | |
|---|---|---|---|
| 0106395 | 4/1984 | European Pat. Off. | 128/395 |
| 3311604 | 10/1983 | Fed. Rep. of Germany | 4/DIG. 10 |
| 118992 | 9/1918 | United Kingdom | 128/369 |

OTHER PUBLICATIONS

Sawerkrop, *Bathing Apparatus*, Dec. 4, 1824.
Yudachi (Advertisement), found in Spa & Sauna Magazine, Jul. 24, 1981; p. 53.

*Primary Examiner*—Edward M. Coven
*Assistant Examiner*—Mark J. Graham
*Attorney, Agent, or Firm*—Robert J. Koch

[57] ABSTRACT

The apparatus includes a basin with a 10–50 cm depth preferably 20 cm and at least a metal halide high pressure lamp (MeH), a mercury high pressure lamp (HgH) or a mercury low pressure lamp (HgN) with filters. The lamps have a spectral range of 290 to 400 nm and are arranged to illuminate prone support surfaces. The bath tub may be made of an acid resistant material, preferably a synthetic plastic. A fixed or removable plastic prone support surface in the tub bottom and a liquid inlet and outlet for circulation of the solution for processing and storage are provided. The outlet is connected to the inlet through a filter device, a processing tank, a thermally insulated storage tank, a thermostatically controlled flow heater and a pumping device. A radiation source may be located under the prone support surface.

28 Claims, 6 Drawing Sheets

BALNEO-PHOTOTHERAPEUTICAL TREATMENT PROCESS AND BATH

This application is a continuation of application Ser. No. 928,086 filed Nov. 7, 1986, abandoned.

BACKGROUND OF THE INVENTION

1. Field of the Invention

The invention relates to a therapeutic treatment apparatus method, for balneo-phototherapeutical treatment of skin or rheumatic diseases and/or the cosmetic or prophylactic treatment of skin, and an apparatus for the embodiment of the process.

2. Description of the Related Technology

In treatment of psoriasis or similar skin diseases a segment of the UV spectrum in the boundary area of UVB and UVA may be used. A wave length of approximately 290 to 330 nm may be utilized. This narrowly limited spectral range contains rays which have sufficient quantum energy for the treatment and penetrate to an adequate depth in the epidermis to reach the lower boundary range of a layer of germs. Microorganisms which cause psoriasis are located in this layer. Radiation of a lower spectral range in the range of UVB radiation is responsible for photodermatosis and must be eliminated to prevent photodermatosis or sunburn.

It was believed that light or radiation with longer wave lengths (above 330 nm) had no antipsoriatric effects. While this is fundamentally correct, light of longer wave lengths has positive supplemental effects which are discussed in more detail below.

Accordingly, apparatuses are known comprising an UV radiation device with a metal high pressure lamp, the filling of which is chosen so that several strongly defined spectral lines in the range between 300 and 330 nm are present. This lamp is a point source of radiation, whereby larger surfaces, for example during the overall irradiation of a patient, may be uniformly irradiated from an adequate distance.

As the result of intensive developments in the field of heliotherapy, at the present time numerous reactions of the organism to application of optical radiation are known. They are generated in part by the affectation of the vegetative nervous system and in part by photochemical reactions of the skin.

The decisive factor for all of these reaction processes is the spectral distribution of radiation energy and the dosage.

While long wave infrared radiation has been recognized as an effective therapy for furunculosis, rheumatism and colds, visible irradiation acting through the eye shows positive effects on the psyche.

The therapeutic application of UV radiation has attained particular importance in numerous skin diseases.

The wave length range of the optical radiation is especially important; it produces changes in the electron shell upon its absorption by the molecule, without initiating any ionization processes. Positive effects may be actuated by irradiation in a wave length range between 300 and 400 nm.

Radiation with wave lengths shorter than 300 nm should not be used for reasons of health and radiation with wave lengths longer than 340 nm shows no effect when applied by itself. In combination with radiation of up to 300 nm there are, however, positive effects.

In recent years numerous so-called tanning studios have been established, equipped with sun beds which may include height adjustable sun canopies. Irradiation of the entire body is possible with this apparatus. The intensive radiation produced by so-called tanning beds is capable of strongly drying the skin thereby causing damage potentially leading to skin cancer. For these reasons, dermatologists disapprove of the use of artifical suns.

The positive effect of baths on the body has been known to mankind since ancient times, especially if the bath is enriched with bath salts and is heated. In this respect, the Dead Sea occupies a special position. Its healing action has been known for thousands of years and, because of its high enrichment in salts of a great variety, its therapeutic action extends to highly different diseases. The problems relating these effects were not investigated in detail until very recently. It was discovered that the Dead Sea has a salt composition that is entirely different from other seas, such as the Mediterranean, the North Sea or the known brine wells. In particular, the proportion of magnesium, potassium and bromine is much higher than in other sea waters. This by itself is, however, not sufficient to explain the therapeutic effect.

SUMMARY OF THE INVENTION

It has been determined that sun light in the area of the Dead Sea differs considerably from total solar radiation, i.e., the radiation reaching a horizontal, flat surface of the earth, coming directly from the sun and being scattered by the atmosphere of the earth. It appears that comparable values in the 300 to 390 nm range are lower than the values of solar radiation. Due to the location of the Dead Sea approximately 400 m below the sea level of the oceans, there is a 400 m thick air layer present having a filter effect not found anywhere else in the world. Threshold values to attain a minimally erythematously effective dosis are therefore higher at the Dead Sea than in the case of total solar radiation.

The invention is based on the discovery that the combination of the effect of the light spectrum of the sun prevailing in the area of the Dead Sea with the specific composition of sea water develops a specific healing force for highly different diseases, in particular diseases of the skin, as may be ascertained by scientific investigations.

The invention is also based on the further discovery that the negative effects of tanning beds and sun canopies used in so-called tanning studios may be avoided by periodically wetting the skin with a liquid containing salts dissolved in water and therefore present in the ionic form. The skin activated by the ions becomes more sensitive to the radiation and absorbs it.

It is an object of the invention to provide a process and an apparatus whereby a patient is exposed to a radiation resembling that prevailing at the Dead Sea, in combination with a bath having a composition corresponding to the composition of the water of the Dead Sea, while drying of the skin by the effect of the radiation is prevented or reduced.

The object is attained by simultaneously exposing the skin of a person being treated to selective rays of one or more radiators or lamps with a spectral wave length range of 290–420 nm in combination with timely interruptions in a salt bath with trace elements having a salt content of 5–20%, preferably 15%, and a temperature of 36° C. or in the range of 20°–38° C., a depth of 10–50 cm preferably 35 cm. The treatment may be for a total time of 10–30 minutes, or in the range of 15–20 minutes.

The radiators and bath may advantageously be arranged such that a reclining surface of the bath apparatus is uniformly illuminated.

In this process the skin of the patient is irradiated in an alternating sequence with a beneficial radiation for a relatively short period of time and immersed immediately thereafter into a liquid and wetted by it.

The skin activated by the radiation preferentially takes up and absorbs the salts present in ionic form during the immediately following bath or wetting phase. The penetration of these minerals, in particular the magnesium and calcium ions advantageously stimulates the formation of the cyclic hormone (AMP) adenylic acid.

According to the invention the composition of the salt may have a salinity of 299.89 and the following ion concentration in mg per liter of water, with +20% tolerance:

| magnesium | 36.15 | chloride | 194.44 |
|---|---|---|---|
| calcium | 13.78 | bromide | 4.56 |
| sodium | 38.51 | sulfate | 0.72 |
| potassium | 7.26 | hydrogen carbonate | 0.23 |
| strontium | 0.24 | other salts | 1.12 |
| lithium | 0.01 | | |

The salt bath has, with a specific gravity of 1.2 to 1.3 in a modified representation, the following composition in g per liter of water, with a +20% tolerance:

| magnesium chloride | 280 | bromine | 8.3 |
|---|---|---|---|
| calcium chloride | 80 | calcium sulfate | 0.1 |
| sodium calcium | 25 | potassium chloride | 23 |

The salt bath apparatus according to the invention may comprise a basin with a depth of 10–50 cm, preferably 20 cm. At least one metal halide high pressure lamp (MeH) and/or a mercury high pressure (HgH) and/or a mercury low pressure lamp (HgN) with filtering devices are located above the bath. The lamps emit radiation with a spectral range of 290 to 400 nm and are arranged such that the prone support positions of the salt bath are irradiated. At least the above three types of lamps are equivalents of a lamp means for generating radiation.

The basin of the salt bath apparatus has a depth of 10 to 50 cm and is followed according to the invention directly or indirectly by a mobile basin, so that kinesitherapy may be applied in combination.

The MeH and/or HgH and/or HgN lamp located above the bath comprises in a further development of the invention filter devices such that maximum radiation is in the range of 380 nm.

All of the above-mentioned types of lamps are equipped according to the invention with filter devices which reduce the UVB component of the effective radiation by at least 2.5 times compared with total solar radiation.

The therapeutic tub may be a reclining tub designed so that the person placed in the tub and irradiated may assume any desired position. The side of the person facing the source of radiation may protrude from the bath liquid. The bath tub may be a single unit with the radiation installation and the horizontal center axis of the radiation installation and the bath tub may be parallel to and located vertically above each other. Advantageously, the distance of the horizontal center axes of the bath tub and the radiation installation may be varied by the height adjustability of the radiation installation.

With the apparatus according to the invention it is possible for a person to expose himself simultaneously to a bath, in particular a salt bath of a specific and adjustable composition, in combination with a specific radiation, wherein the brine may be maintained at the temperature required by continuous or periodic circulation.

In a further development of the invention the salt bath apparatus comprises a bath tub made of an acid resistant material, preferably a synthetic plastic material. A fixedly installed or removable prone support, preferably made of a plastic material, is provided over the bottom of the tub. A liquid inlet in the head area of the bath tub and a liquid outlet in the foot area are provided to circulate the salt solution through a processing and storage installation.

In case of a fixed or permanent installation of the prone support in the bath tub, it is advantageous to provide a pump in the bottom of the bath tub underneath the prone support. The pump may be connected to a thermostatically controlled heating device. It is thus possible to circulate the salt solution in the tub without a central installation.

Individual treatment in an institute, a clinic or in the private sector is made possible by this measure.

According to the invention, the liquid outlet of the bath tub may be connected to the liquid inlet of the bath tub through a preparation tank, a thermally insulated storage tank, a thermostatically controlled flow heater and a pumping device. Accordingly, the relatively expensive salts may be purified and processed for a successive bath in accordance with provisions of the law or applicable health codes.

The spectral flux distribution of a lamp-reflector-filter combination or means for generating radiation may comprise interchangeable filters to adapt radiation or adjust wave length to a particular range to achieve a desired biological action.

In a further development of the invention the preparation tank of a central installation may be connected to a fresh water supply line and a waste water drain by controllable valves. The salt bath may thus be prepared with the desired concentration and processed after use. The salt bath is continuously monitored for its salt content using known monitoring techniques and the salt content regulated accordingly.

According to the invention an economically operating installation may be produced for use in clinics or bath houses. It is advantageous to connect a number of bath tubs in parallel to the processing and storage tanks. In this manner all of the equipment for preparation of the salt bath and processing of the used bath water, including the filtering device may be laid out and operated centrally, thereby effecting economical operation of the installation.

According to the invention a bath tub may be mounted on rollers. Certain components may be integrated with the tub, for example, pumps and filters may be built in below or installed directly adjacent to the tub.

The radiation sources placed over the bath tub may be adjustable in height.

According to the invention the UVB component of the effective radiation is limited. The maximum value of the erythemously effective radiation intensity should not exceed 0.028 $W/m_2$ as specified in the DIN (German Industrial Standard) standard. Accordingly, the UVB radiation is reduced by a factor of 2.5 by filtering. The values obtained simultaneously approximate those prevailing in the vicinity of the Dead Sea.

In general the propensity of a light source to cause sunburn may be determined by comparing its radiation with natural solar radiation (global radiation). The photobiologically effective radiation intensity of solar radiation depends on the season, the geographic latitude and the height of the sun. The maximum solar radiation at noon in the area of the southern Mediterranean is used for comparison. The maximum value of the erythemously effective radiation intensity of solar radiation according to DIN 5050 for a 90° height of the sun is 0.28 W/m$^2$. A limitation of the erythemously effective radiation intensity of a UV irradiation apparatus to 1/10 of this value results in attainment of erythemously effective threshold radiations after a period of about 15 min. for individuals with sensitive skin.

BRIEF DESCRIPTION OF THE DRAWINGS

The invention will become more apparent from the description below of the drawings attached hereto. In the drawings.

DETAILED DESCRIPTION OF THE PREFERRED EMBODIMENT

Figure 1:
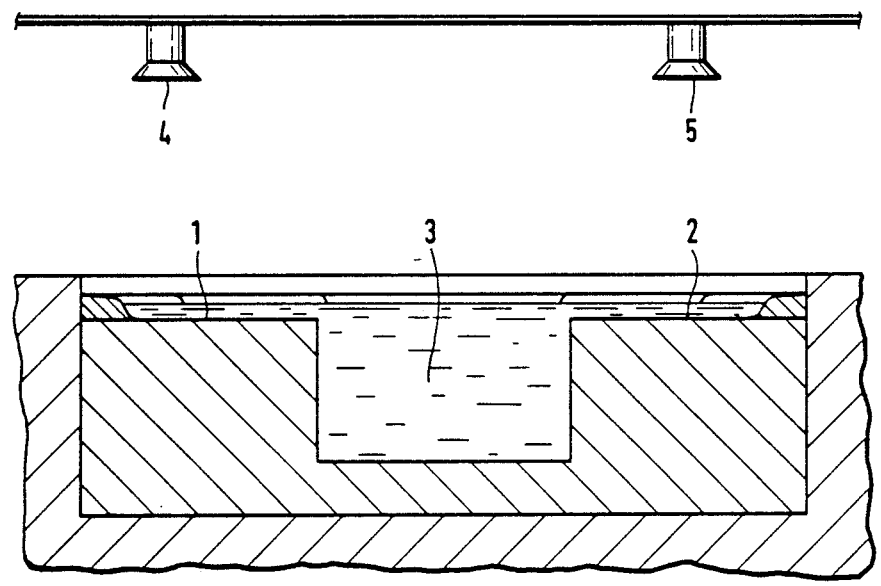
FIG. 1 shows a cross section of a basin for a salt bath with an integrated mobile basin and a layout of the lamps or radiators above the prone or reclining support surfaces provided in an oval configuration around the mobile basin, in the schematic view.

FIG. 1 shows in cross section a salt bath apparatus having a flat basin 1 having a depth of 10–50 cm and a mobile or mobility basin 3, directly connected with the flat basin.

Located on the opposite side of the basin 1 is another flat basin 2 in the form of a prone or reclining support surface. A plurality of metal halide high pressure lamps (MeH) 4, 5, 6 and 7 are arranged above the salt bath apparatus, which could also include mercury high pressure (HgH) and/or mercury low pressure (HgN) lamps. The lamps are equipped with filter devices, not shown, permitting the passage of a spectral range of 290 to 400 nm. The layout of the lamps is such that the prone support surfaces 1 and 2 of the salt bath are illuminated.

The depth of the mobile basin 3 is approximately 1.20 to a maximum of 1.50 m, so that a person may stand upright in the basin. The salt solution with a specific gravity of 1.2 to 1.3 has a correspondingly favorable buoyancy so that the person's joints are completely relieved of the weight of the body during kinesitherapy. The patient may expose himself for predetermined time intervals to the radiation of the lamps 4 to 7 by moving to the flat basin. The depth of this basin is such that in a prone position, the upper parts of a patient's body protrudes from the bath, thereby making direct irradiation possible. By regularly wetting the skin or by the turning of the body, a periodic wetting of the skin during the irradiation with a liquid containing salts dissolved in water and thus present in the ionic form is accomplished. The skin activated by the irradiation therefore takes up the salts present in the form of ions preferably and absorbs them, as mentioned above, without drying out the skin.

Figure 2:
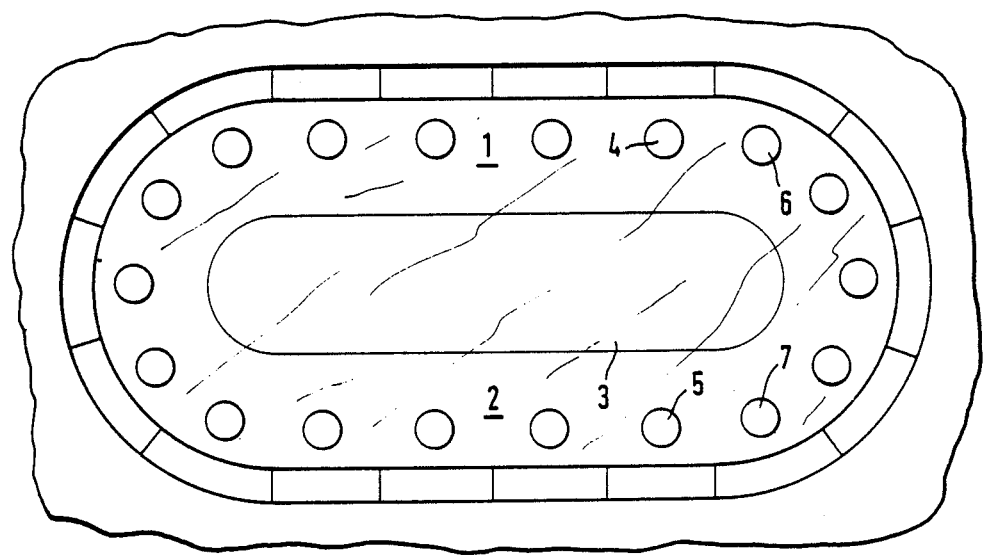
FIG. 2 shows a top view of a basin for a salt bath with an integrated mobile basin and a layout of the lamps over the prone support surfaces according to FIG. 1, in a schematic view.

FIG. 2 shows a top view according to FIG. 1, in which it is seen that the prone support surfaces 1 and 2 form a closed surface and surround the mobile basin 3. The balneo-phototherapeutic treatment in this embodiment may be combined with kinesitherapy.

Figure 3:
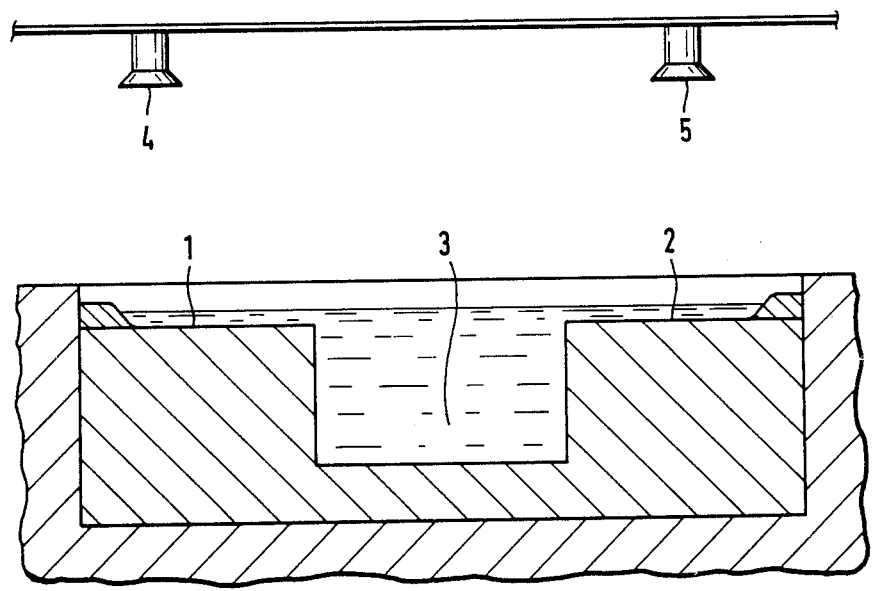
FIG. 3 shows a cross section of a basin for a salt bath with an integrated mobile basin and a layout of the lamps over the prone support surface located parallel to the mobile basin, in a schematic view.
Figure 4:
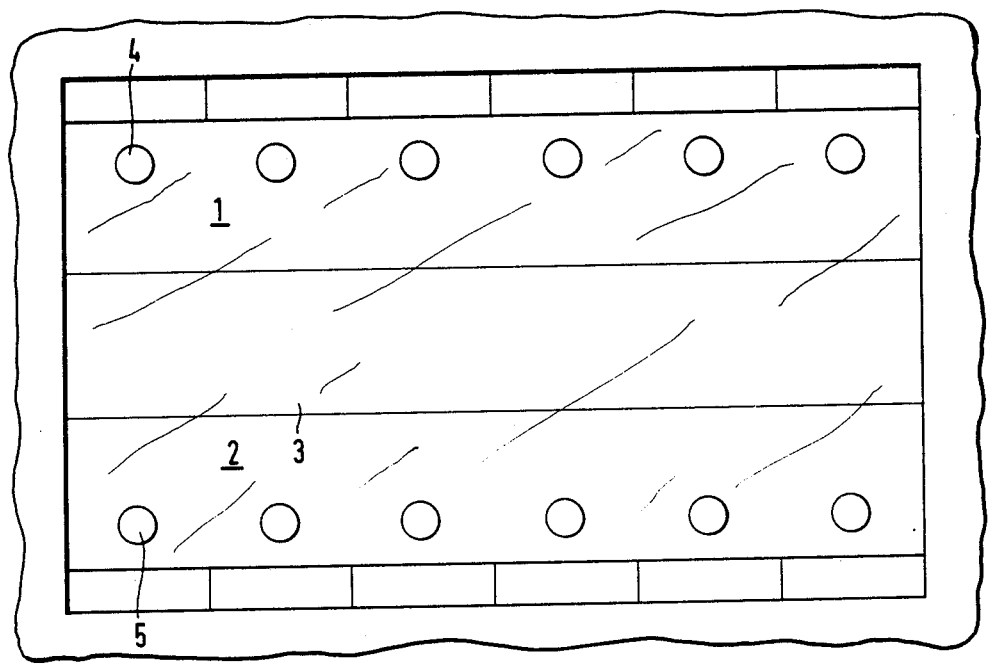
FIG. 4 shows a top view of a basin for a salt bath with an integrated mobile basin and a layout of the lamps over the prone support surfaces according to FIG. 3, in a schematic view.

FIGS. 3 and 4 show a modified embodiment of the geometric configuration of the prone support surfaces in relation to the mobile basin. The prone support surfaces 1 and 2 here are located parallel to each other and to the mobile basin. In FIGS. 3 and 4 identical elements are designated by identical reference symbols.

Figure 5:
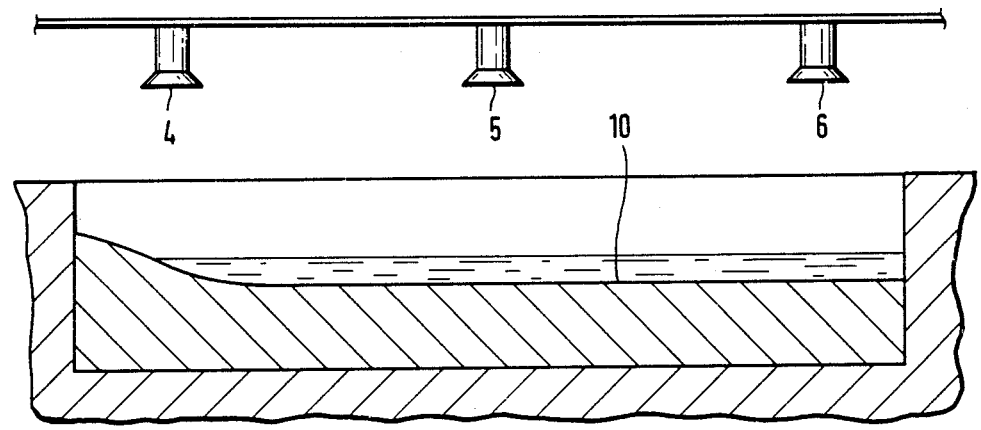
FIG. 5 shows a cross section through a prone support in the form of a basin.
Figure 6:
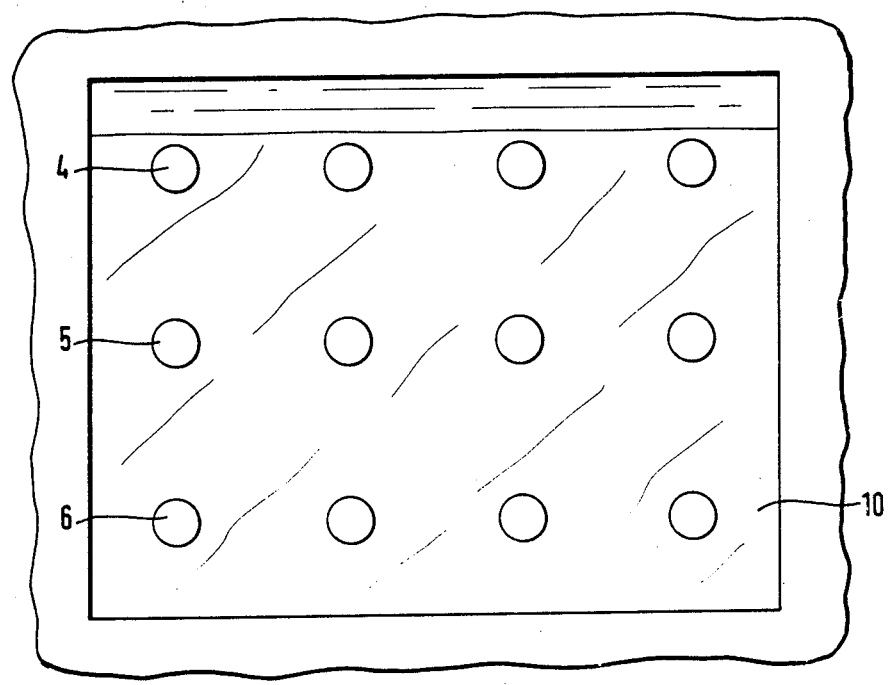
FIG. 6 shows a top view of a prone support surface in the form of a basin according to FIG. 5.

FIGS. 5 and 6 show a flat basin 10 in cross section (FIG. 5) and in a top view (FIG. 6) which is designed as a prone surface only and has a depth of 10 to 50 cm. The lamps 4, 5 and 6 and the adjacent rows of lamps, not shown in detail, uniformly illuminate the prone support surfaces of the basin 10.

Figure 7:
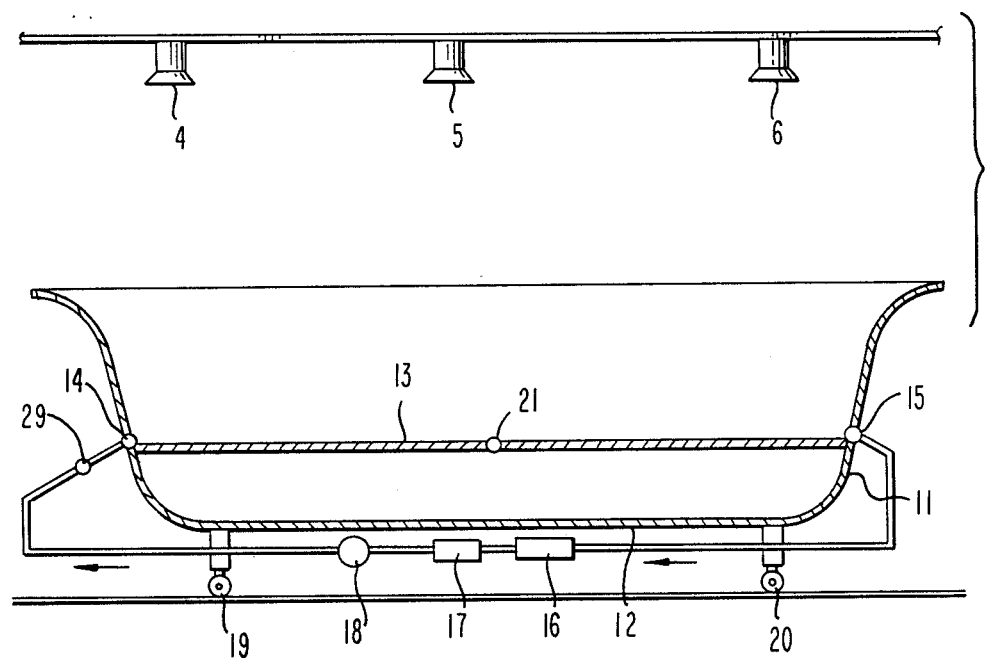
FIG. 7 shows a cross section through a bath tub according to the invention.

FIG. 7 shows a further embodiment of the invention in the form of a mobile salt bath apparatus to carry out the process according to the invention.

This apparatus includes a bath tub 11, made of an acid resistant material, preferably a synthetic plastic. A prone support surface 13 is arranged above the bottom 12 of the tub. An inlet 14 for a liquid is provided in the head area of the tub and an outlet 15 for the liquid in the foot area of the tub 11. The inlet 14 and outlet 15 are connected with each other through a heat exchanger 16, a filter device 17 and a pump 18. The lamps 4, 5 and 6 are adjustable in height in a manner not shown in detail, whereby the radiation density on the surface to be irradiated may be varied.

Directly under the prone support surface 13, in a further embodiment not shown in detail, additional sources of radiation may be arranged, if the prone support surface 13 is made, for example, of an acrylic glass.

Installations such as that shown in FIG. 7 are used preferably and advantageously in the private sector.

In the detailed layout of a bath tub intended for private use, the individual elements or components of the system may be placed directly under the tub. This includes, for example pumps, filters, heating devices and valves.

The bath tub 11 may be supported on rollers 19, 20 and the liquid inlet 14 and outlet 15 in this case may be equipped with mobile hose connections, not shown in detail.

For commercial use, several tubs are installed in separate rooms and are supplied with bath water centrally by the used water processing installation.

Figure 8:
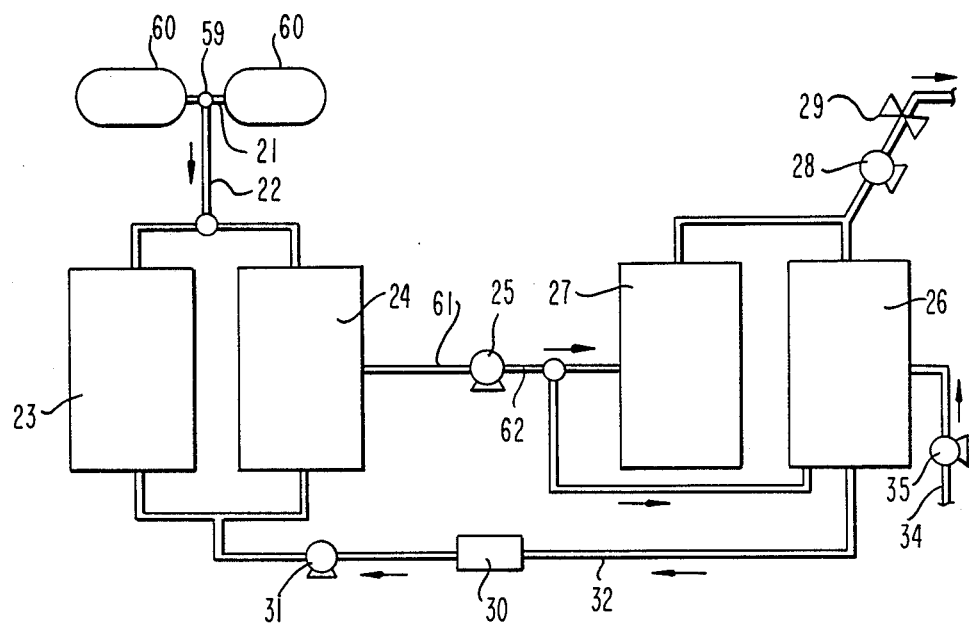
FIG. 8 shows a schematic view of a central installation including the devices required for filtering, processing, storage and transport.

FIG. 8 shows an installation for processing used water. The used water of a single basin or several bath tubs 60 flows from the drain pipe 21 through valves 59 and feeder line 22 to used water tanks 23, and 24. Tank 23 is connected in parallel with used water tank 24. A pump and filter combination 25, move filtered salt solution from lines 61 to line 62 into the corresponding storage tanks 26 and 27, which again are connected in parallel. The salt solution is supplied to the tube or tubes as needed by means of a pump 28 through the line 29, for example, through the liquid inlet 14 to a bath tub 11 (FIG. 7) at the temperature required. When the tub 11 is full, a magnetic valve in line 29 (FIG. 7) shuts the flow off. There is a continuous recirculation from the used water processing installation tank 27 through the line 32, the thermostatically controlled heating device and into the tanks 23 and 24. The circulation is aided by pump 31. By this arrangement the salt solution is constantly reprocessed. The processing tanks 26 and 27, respectively, are connected with a fresh water supply line 34 which assures a constant water level by a magnetic valve 35.

The salt content is continuously monitored in the processing tank, so that the bath salts may be replenished as needed.

The storage tank 26 and 27 always contain a salt solution prepared in accordance with health regulations in sufficient volumes to supply the existing number of basins or tubs.

Figure 9:
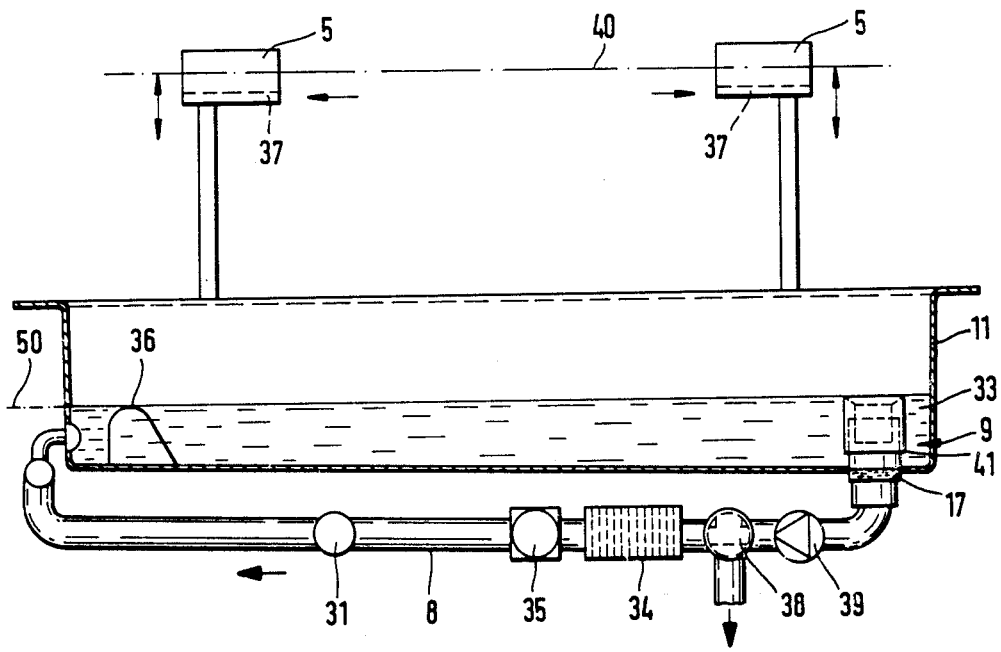
FIG. 9 shows a cross section through a bath apparatus according to the invention.
Figure 10:
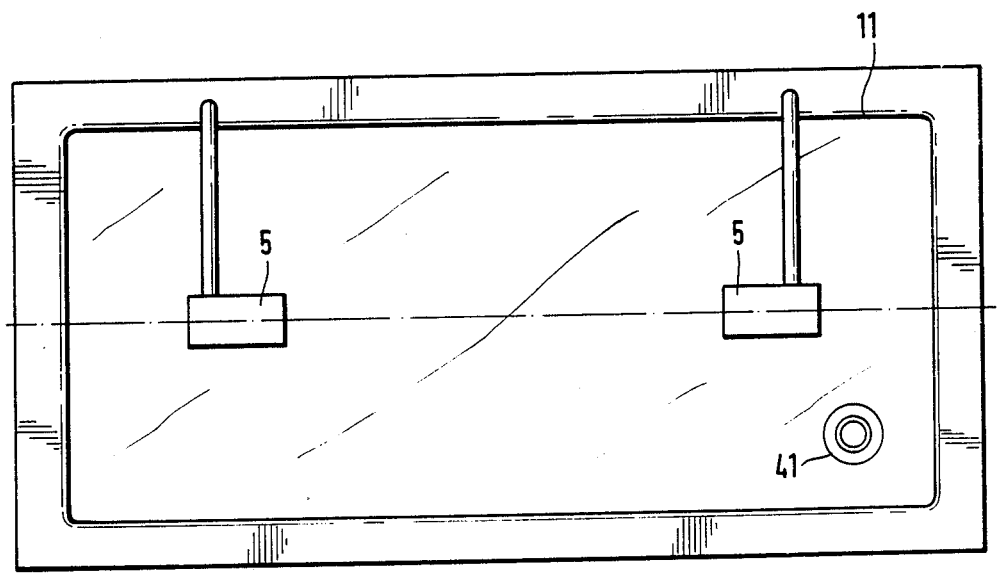
FIG. 10 shows a top view of the bath apparatus according to FIG. 9.

Following the filling of a bath tub 11, its own circulating apparatus is actuated by means of a switch 33 (FIG. 9). Pump 18 pumps the salt water through the heating installation 16, thereby maintaining the water at a constant temperature for the user. After use, the tub is drained through the line 21, wherein the water is pumped or flows by gravity to the tanks 23 or 24 (FIG. 8) to be reprocessed.

FIG. 9 shows an alternative embodiment of the invention. A therapeutic tub is designed so that the person present in the bath and to be irradiated is able to assume; any desired position, such that the side of the person facing the sources of radiation 5 protrudes from the bath liquid 33.

The bath tub 11 and the radiation installation or the sources of radiation 5 are a single unit. The radiation sources 5 may be arranged and adjusted to a maximum degree with respect to the distribution of their radiation.

The horizontal center axis 40 of the entire radiation installation 5 and the horizontal center axis 50 of the bath tub are advantageously parallel and located vertically above each other. The distance of the horizontal center axis 50 from the bath tub 11 and the center axis 40 of the radiation installation is variable as the radiation installation 5 is height adjustable.

The bath tub 11 is flat in the longitudinal direction and has a head rest 36. The head rest 36 may be height adjustable.

The spectral radiation flux distribution of the lamp-reflector-filter assembly of the radiation installation 5 comprises a plurality of interchangeable filters for adaptation to a desired biological effect.

The distribution of the radiators above the bath apparatus 11 in the longitudinal direction is such that a uniform distribution of the radiation intensity in the useful plane, i.e. at a short distance over the liquid level of the bath tub 11, is obtained.

A circulation path 8 is provided for continuous circulation of the bath liquid or brine 33, comprising a level control 41, a filter 17, a pump 31, a heater 34, a disinfecting device 35, a preferably remotely controlled three-way cock 38 and a preferably remotely controlled valve 39. The disinfecting device 35 advantageously contains a UV apparatus.

Figure 11:
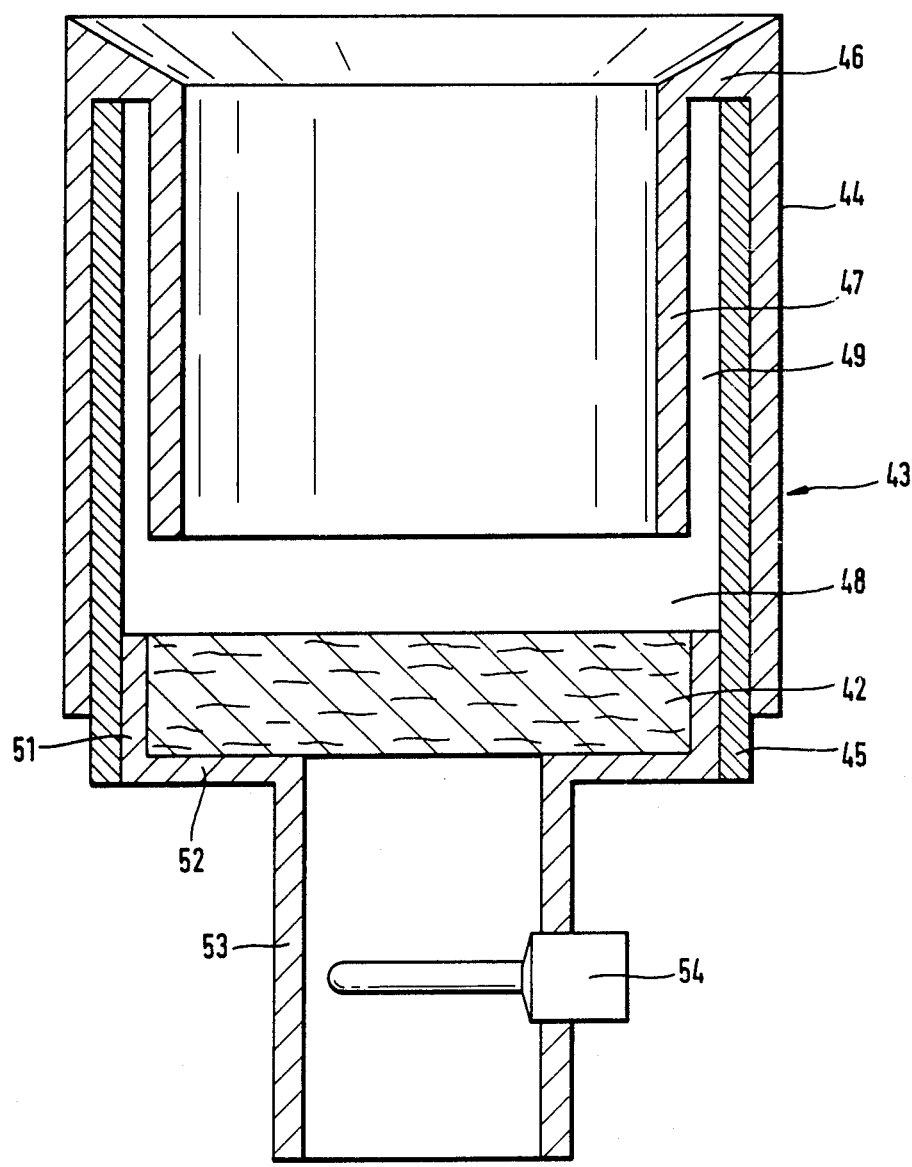
FIG. 11 shows an enlarged view of a height adjustable level overflow control.

FIG. 11 shows in an enlarged view of an embodiment of a level control 43 which may be installed as level control 41. The control adapts the liquid level in the bath tub 11 to the displacement of water by the person treated. The level control 41 is located at the tub outlet and contains the purification filter 17 of the water circulation (designated in FIG. 11 by 42).

The level control device 43 is designed so that it conducts the bath liquid from the surface to the water circulation path.

The level control device 43 comprises an external tube 44 in which a further tube 45 is slidingly located. A closing ring 46 is fastened to the upper end of the tube 45. A tube 47 is connected to the inside of the closing ring. A gap 48 open to an air jacket 49 is left at a lower end of tube 47.

The air jacket 49 is thus bordered by the tube 45, the closing ring 46 and the tube 47.

A tube fitting 51 is fastened to a bottom ring 52 which is connected to an outlet ring 53, which may be threaded. A filter 42 is arranged in the tube fitting 51. The filter 42 may be supported on a perforated disk, not shown. A heat sensor 54 is located in the outlet ring 53.

If the liquid flow through the outlet ring 53 is blocked, the liquid rises in the tube 47 and the space of the air jacket 49. This air is compressed, increases its pressure and raises the closing ring 46 together with the tube 47 connected with it, so that a higher water level is attained in the tub.

The heater 34 (FIG. 9) is located in the brine circulation path 8 and may be an electric resistance heating device. The brine is heated to the temperature set by the thermostat, with the brine serving as a conductor for the electric resistance heater.

The invention provides a process and means which are useful not only in clinics for the successful treatment of skin diseases, such as psoriasis, acne, ichthyosis (fish scale disease), psoriasis of the scalp, neurodermatisis, but also in private home treatments.

The process and the apparatus are also suitable for beauty treatments, as in the case of the known tanning beds where the skin dries out easily. By means of the periodic wetting with the salt solution the skin is advantageously activated, so that not only the drying of the skin is prevented but also the skin and the body are supplied through the skin with important salts.

I claim:
1. A treatment apparatus comprising:
   a salt bath basin containing a salt solution exhibiting a prone support surface at a depth of 10–50 cm, below a surface of said salt solution and a liquid outlet;
   means for emitting light radiation having a spectral wavelength of 290–420 nm arranged to irradiate said prone support surface;
   means for processing said salt solution which is connected to said liquid outlet, wherein said means for processing: (a) filters the salt solution from said liquid outlet, (b) controls the temperature of said salt solution, and (c) controls the salt bath composition of said salt solution means for filling said salt bath basin with processed solution from said means for processing.

2. A treatment apparatus according to claim 1, wherein said salt bath basin further comprises a mobility basin having a greater depth than said prone support surface.

3. A treatment apparatus according to claim 1, wherein said means for emitting light radiation comprises a lamp means for generating radiation and a means for filtering said radiation.

4. A treatment apparatus according to claim 3, wherein said means for filtering passes radiation only in the area of 380 nm.

5. A treatment apparatus according to claim 3, wherein said means for filtering reduces a UVB component of effective radiation compared with total solar radiation by a factor of at least 2.5.

6. A treatment apparatus according to claim 3, wherein said salt bath basin further comprises a bath tub made of an acid resistant material and said prone support surface is removably installed above the bottom of the tub and made of a synthetic plastic.

7. A treatment apparatus according to claim 1, wherein said salt bath basin further comprises a bath tub made of an acid resistant material, and said prone support surface being fixedly installed above the bottom of the tub and made of a synthetic plastic.

8. A treatment apparatus according to claim 7, further comprising a pump connected to a thermostatically controlled heating device beneath said prone support surface.

9. A treatment apparatus according to claim 6, wherein said means for processing said salt solution comprises a filter device, a processing tank, a thermally insulated storage tank, a thermostatically controlled flow heater and a pumping device connected to a liquid inlet means in said basin.

10. A treatment apparatus according to claim 9, further comprising a controllable valve in a fresh water feeder line and a second controllable valve in a drain line, each of said lines being connected to said processing tank.

11. A treatment apparatus according to claim 9, further comprising at least one additional bath tub, said bath tubs being connected in parallel feed arrangement with respect to each other and in parallel with respect to said means for processing and storage by way of intermediate valves.

12. A treatment apparatus according to claim 3, further comprising tubs supported on rollers for supporting said bath basin.

13. A treatment apparatus according to claim 3, wherein said lamp means is arranged above said basin.

14. A treatment apparatus as in claim 13, wherein said lamp means is mobile.

15. A treatment apparatus according to claim 14, wherein said lamp means is adjustable in height.

16. A treatment apparatus according to claim 3, wherein said prone support surface is clear and a lamp means is located beneath said prone support surface.

17. A treatment apparatus according to claim 7, wherein said prone support surface is clear and a lamp means is located beneath said prone support surface.

18. A treatment apparatus according to claim 12, wherein said prone support surface is clear and a lamp means is located beneath said prone support surface.

19. A treatment apparatus according to claim 7, wherein said means for processing said salt solution comprises: a filter device, a processing tank, a thermally insulated storage tank, a thermostatically controlled flow heater and a pumping device connected to a liquid inlet means in said basin.

20. A treatment apparatus according to claim 19, further comprising a controllable valve in a fresh water feeder line and a second controllable valve in a drain line, each of said lines being connected to said processing tank.

21. A treatment apparatus according to claim 19, further comprising at least one additional bath tub in particular bath tubs connected in parallel with respect to each other and to said means for processing and storage by means of intermediate valves.

22. A treatment apparatus according to claim 1, wherein the salt solution exhibits a salinity of 299.89 and has an ion concentration, in mg per liter of water, with +20% tolerance of:

| magnesium | 36.15 | chloride | 194.44 |
|---|---|---|---|
| calcium | 13.78 | bromide | 4.56 |
| sodium | 38.51 | sulfate | 0.72 |
| potassium | 7.26 | hydrogen carbonate | 0.23 |
| strontium | 0.24 | other salts | 1.12 |
| lithium | 0.01 | | |

23. A treatment apparatus according to claim 1, wherein the salt solution exhibits a specific gravity of 1.2 to 1.3 and has a composition in g per liter of water, with +20% tolerance of:

| magnesium | 280 | bromine | 8.3 |
|---|---|---|---|
| calcium | 80 | calcium sulfate | 0.1 |
| sodium chloride | 25 | potassium chloride | 23 |

24. A treatment apparatus comprising:
a salt bath containing a salt solution at a temperature of about 36 degrees centigrade, and exhibiting a center axis, a prone support surface at a depth of about 20 cm below a surface of said salt solution, a liquid outlet, and a liquid inlet;
filtered lights emitting light radiation having a spectral wavelength of 290–420 nm, a uvb component equal to that of total solar radiation reduced by a factor of at least 2.5 times, and a maximum value of erythemously effective radiation equal to 0.028 Watts per square meter, said filtered lights arranged on a horizontal axis parallel to the center axis of said bath to irradiate said prone support surface;
a pump for recirculating said salt solution from said liquid outlet through a heat exchange and a filter device to said liquid inlet.

25. A treatment apparatus according to claim 24, wherein said salt solution exhibits a salinity of 299.89 and an ion concentration, in mg per liter of water with a 20% tolerance, of:

| bromide | 4.56 |
|---|---|
| calcium | 13.78 |
| chloride | 194.44 |
| hydrogen carbonate | 0.23 |

| -continued | |
|---|---|
| lithium | 0.01 |
| magnesium | 36.15 |
| other salts | 1.12 |
| potassium | 7.26 |
| sodium | 38.51 |
| strontium | 0.24 |
| sulfate | 0.72 |

26. A treatment apparatus comprising:

a salt bath containing a salt solution at a temperature of about 36 degrees centigrade, and exhibiting a center axis, a prone support surface at a depth of about 20 cm, a liquid outlet, and a liquid inlet;

filtered lights emitting light radiation having a spectral wavelength of 290–420 nm, a uvb component equal to that of total solar radiation reduced by a factor of at least 2.5 times, and a maximum value of erythemously effective radiation equal to 0.028 Watts per square meter, said filtered lights arranged on a horizontal axis parallel to said center axis of said bath to irradiate said prone support surface;

a line connecting said bath to a used water tank;

a combination pump and filter connected from said used water tank to a storage tank;

a second pump connecting said storage tank to said used water tank;

a third pump connecting said storage tank to said bath; and a line connecting a fresh water source to said storage tank.

27. A treatment apparatus according to claim 26, wherein said salt solution exhibits a salinity of 299.89 and an ion concentration, in mg per liter of water with a 20% tolerance of:

| bromide | 4.56 |
|---|---|
| calcium | 13.78 |
| chloride | 194.44 |
| hydrogen carbonate | 0.23 |
| lithium | 0.01 |
| magnesium | 36.15 |
| other salts | 1.12 |
| potassium | 7.26 |
| sodium | 38.51 |
| strontium | 0.24 |
| sulfate | 0.72 | and further comprising:

means for continuously monitoring said temperature, said salinity, and said ion concentration of said salt solution in said processing tank.

28. A treatment apparatus according to claim 27, further comprising a plurality of said salt baths, wherein said salt baths are connected in parallel with respect to each other and in parallel with respect to said used water and storage tanks by means of intermediate valves.

* * * * *